US 6,693,089 B1

(12) United States Patent
Li et al.

(10) Patent No.: US 6,693,089 B1
(45) Date of Patent: *Feb. 17, 2004

(54) REDUCING ADHESION

(75) Inventors: Jianmin Li, Lexington, MA (US); Weenna Bucay-Couto, Bedford, MA (US); Timothy P. Harrah, Newton, MA (US)

(73) Assignee: SciMed Life Systems, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/339,905

(22) Filed: Jan. 10, 2003

Related U.S. Application Data

(63) Continuation of application No. 09/791,490, filed on Feb. 23, 2001.
(60) Provisional application No. 60/185,223, filed on Feb. 25, 2000.

(51) Int. Cl.[7] .............................................. A61K 31/715
(52) U.S. Cl. .............................................. 514/54; 536/3
(58) Field of Search ................................ 514/54; 536/3

(56) References Cited

U.S. PATENT DOCUMENTS

| | | | |
|---|---|---|---|
| 4,897,349 A | 1/1990 | Swann et al. ............... 435/101 |
| 4,920,104 A | 4/1990 | DeVore et al. ................. 514/54 |
| 5,149,331 A | 9/1992 | Ferdman et al. ............. 604/290 |
| 5,266,326 A | 11/1993 | Barry et al. ................. 424/423 |
| 5,356,883 A | 10/1994 | Kuo et al. .................... 514/54 |
| 5,443,473 A | 8/1995 | Miller et al. ................. 606/166 |
| 5,502,081 A | 3/1996 | Kuo et al. .................... 514/777 |
| 5,532,221 A | 7/1996 | Huang et al. .................. 514/53 |
| 5,621,093 A | 4/1997 | Swann et al. ............... 536/55.2 |
| 6,150,581 A | 11/2000 | Jiang et al. .................... 602/50 |

FOREIGN PATENT DOCUMENTS

EP   0 380 254   8/1990

OTHER PUBLICATIONS

Seprafilm Package Insert [online ]. Genzyme Corporation, Cambridge, MA, USA [retrieved on Feb. 22, 2001 ]. Retrieved from the Internet: <URL: http//www.genzymebio-surgery.com/opage.asp?ogroup=1&olevel=4&opage=75>.

*Primary Examiner*—Peter O'Sullivan
(74) *Attorney, Agent, or Firm*—Testa, Hurwitz & Thibeault, LLP

(57) ABSTRACT

A method of reducing adhesion at a site of trauma includes forming a film from an alginate solution, contacting the film with a cross-linking solution to form a cross-linked mechanically stable sheet, and placing at least a portion of the sheet at the site of trauma. An anti-adhesion barrier includes a sheet of ionically cross-linked alginate having a thickness in a range of 0.25 mm to 10 mm. The sheet has a tear strength sufficient for suturing and repositioning. A drug delivery device includes a cross-linked alginate container that can be filled with a drug.

24 Claims, 5 Drawing Sheets

REDUCING ADHESION

CROSS-REFERENCE TO RELATED CASE

This application is a continuation of U.S. application Ser. No. 09/791,490, filed Feb. 23, 2001, and claims the benefit of and priority to U.S. Provisional Patent Application Serial No. 60/185,223, filed Feb. 25, 2000. The entirety of both of is incorporated herein by reference.

TECHNICAL FIELD

The invention generally relates to polymer medical devices for insertion into a body.

BACKGROUND INFORMATION

Surgery or injury often leads to the problem of tissue adhesion. For example, injury, incision or abrasion of the peritoneum, pleural or abdominal cavity causes release of a serosanguinous exudate. The exudate coagulates, which leads to production of fibrinous bands between abutting surfaces. These bands can organize by fibroblast proliferation to become collagenous adhesions.

Adhesions can also form at sites of bone fractures. Bony spurs promote the formation of fibrous adhesions between the fracture site and neighboring tissue. Surgery caused adhesions are generally undesirable. For example, adhesions can impair normal movement between bones and tendons, cause bowel obstructions and disrupt nerve transmissions.

Approaches to reduction of post-surgical adhesion include the application of drugs or surfactants, and use of collagen, collagen-fabric, collagen membranes or reconstituted collagen as physical barriers. Other barriers are made from polyester, collagen, amino acids polymers and chitin.

In situ methods of barrier formation have utilized carboxyl-containing polysaccharides. Barriers can consist of a polysaccharide solution, covalently cross-linked polysaccharide or ionically cross-linked polysaccharide.

Hyaluronic acid ("HA") is a polysaccharide that has been used for anti-adhesion applications. To provide greater stability, HA can be cross-linked in a patient with a number of ionically cross-linking solutions, such a ferric chloride solution. Alginate is another polysaccharide that can be used for anti-adhesion purposes. The barrier is formed at a desired site by simultaneous spraying of polysaccharide solution and cross-linking solution, injection of solutions or spreading a foam or gel at the site.

SUMMARY OF THE INVENTION

The invention generally involves low cost, easy to place and reposition anti-adhesion barrier sheets. Prior methods and devices for reduction of trauma site adhesion have several deficiencies. In situ formation of barriers creates the need for use of more equipment and expenditure of more time and effort by a medical worker. In situ formation also leads to a barrier of variable properties. The exact degree of cross-linking, thickness of a material, and location of the material will vary from patient to patient. Prior methods of use of cross-linked polysaccharides prevent easy removal of barrier material from a patient. Though much used, HA is very expensive and provides barriers of limited physical stability and lifetime.

The invention also generally involves adhesion barriers that have low cost and are easy to use. Adhesion barriers according to the invention do not require in situ formation, have a lifetime in a body of up to two weeks or more, and permit a medical worker to both reposition and fix the barrier at a desired location. The invention generally relates to a repositionable, long life, low cost barrier sheet that a medical worker can suture to tissue. The invention also generally relates to a container-based drug delivery device.

In one aspect, the invention features a device for insertion into a body to reduce adhesion. The device comprises a sheet comprising ionically cross-linked alginate. The sheet has sufficient mechanical stability to allow suturing of the sheet to a body tissue. The sheet provides a barrier to reduce adhesion between the body tissue and a neighboring body tissue.

In one embodiment, the sheet has a thickness in a range of 0.25 mm to 10 mm. In a further embodiment, the sheet has a tear strength in a range of 5 psi to 500 psi. In a further embodiment, the sheet can be fabricated, or cut by a medical worker, in a variety of shapes, including a polygon, an oval and a disk. In another embodiment, more than 25 wt % of the sheet is water.

In one embodiment, an outer portion of the sheet has a lower density of cross-linking relative to an inner portion of the sheet. In a further embodiment, the device includes a suture for tying the sheet to a tissue.

In another aspect, the invention features a drug delivery device for insertion in a body. The device comprises a container that comprises mechanically stable ionically cross-linked alginate. In one embodiment, the container is filled with one or more drugs and inserted in a body.

In one aspect, the invention features a method of forming a sheet for use as an adhesion barrier. The method comprises forming a film from an alginate solution, and contacting the film with a cross-linking solution to form a cross-linked mechanically stable sheet. At least a portion of the sheet can be placed at a site of trauma to create the adhesion barrier. In one embodiment, the method includes suturing the portion of the sheet to secure it to the site of trauma.

In one embodiment, the method further comprises selecting a quantity of the alginate solution to yield a sheet having a thickness in a range of 0.25 mm to 10 mm. In another embodiment, contacting comprises waiting a preselected period of time to obtain a preselected density of cross-linking. In one embodiment, the alginate film is stored prior to contacting with the cross-linking solution.

In one embodiment, contacting is accomplished by pouring. In another embodiment, contacting is accomplished by spraying. In still another embodiment contacting is accomplished by extrusion of the film of alginate solution into a bath of cross-linking solution.

In one embodiment, the film from an alginate solution is formed by dipping a substrate into a bath of the alginate solution. In another embodiment, contacting is accomplished by dipping the substrate in a bath of the cross-linking solution.

In a further embodiment, the cross-linked mechanically stable sheet is contacted with an ion stripping agent to reduce a density of cross-linking in an outer portion of the sheet relative to an inner portion of the sheet.

In one embodiment of the invention, the alginate solution comprises water and a water soluble alginate selected from the group consisting of sodium alginate, potassium alginate, magnesium alginate or propylene glycol alginate.

In one embodiment, the cross-linking solution comprises a divalent or trivalent metal salt. The salt can be, for example, a salt of barium, calcium, copper, cobalt, aluminum, iron, boron, beryllium, lead or silver. In another embodiment, the alginate solution comprises alginic acid having an active ester or aldehyde at a carboxylate site, and the cross-linking solution comprises a bifunctional cross-linker.

In another embodiment, the alginate solution comprises a filler. The fillers can be radiopaque materials to allow visualization of the barrier within the body, both during and after placement at a desired target site. The fillers can be materials that increase the mechanical strength of the barrier, for example pieces of non-dissolvable polymer material, such as suture material, or other non-dissolvable materials. In another embodiment, the filler is a lifetime enhancer that comprises a sulfate of calcium, barium, strontium, copper, zinc or iron.

In another embodiment, the alginate solution includes one or more polymers selected from the group consisting of a biodegradable polymer, a polysaccharide, a polyester and a polymer with covalent cross-linking. The polymers are selected to modify the elastic modulus and hydrophobicity of the sheet.

In another embodiment, the alginate solution comprises an additive for medical treatment, for example, an antiseptic, an antibiotic, an anticoagulant, a contraceptive, a nucleic acid molecule, a protein, and a medicine. In another embodiment, the alginate solution comprises a biocompatible dye to assist observation of sheet location in a body. In other embodiments of the invention, a filler or other additive is included in the cross-linking solution.

In another aspect, the invention provides a method of making a drug delivery device for insertion in a body. The method comprises forming a film from an alginate solution, and contacting the film with a cross-linking solution to cross-link an outer portion of the film. An interior portion of the film remains substantially non-cross-linked and is drained through an opening in the outer portion. In one embodiment, the outer portion is then filled with one or more drugs and inserted in a body. In another embodiment, the method further comprises inserting cross-linking solution into the drained outer portion to further cross-link the outer portion.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1a shows formation of a film. FIG. 1b shows contacting the film with a cross-linking solution. FIG. 1c shows allowing contact to continue for a period of time. FIG. 1d shows a mechanically stable, cross-linked sheet.

FIG. 6a shows a cross-linked sheet. FIG. 6b shows contact with an ion-stripping agent. FIG. 6c shows a sheet having greater cross-link density in an inner portion than in outer portions.

FIG. 7a shows a film that has received partial cross-linking to form a container filled with substantially non-cross-linked material. FIG. 7b shows draining the substantially non-cross-linked material through an opening in the container.

DESCRIPTION

This invention relates to polymer medical devices for insertion into a body and methods for making such devices. More particularly, the invention relates to cross-linked alginate barriers for reduction of post-surgical body tissue adhesion. The medical devices according to the invention are suitable for both human and animal use.

In one aspect, the invention provides a mechanically stable cross-linked alginate-based sheet that is fabricated and stored prior to use as a barrier in a body. A medical worker places the sheet at a desired location in the body to reduce post-trauma adhesion at the location. In another aspect, the invention provides a cross-linked alginate-based container for drug delivery inside of a patient.

A site of trauma is here understood as a site of tissue injury that includes, though is not limited to, sites of incision, drying, suturing, excision, abrasion, contusion, laceration, anastomosis, manipulation, prosthetic surgery, curettage, orthopedic surgery, neurosurgery, cardiovascular surgery, and plastic or reconstructive surgery. Sites of trauma are also here understood to include neighboring undamaged tissue.

The invention has application in various surgical procedures, such as: 1) gynecological (myomectomy via laparotomy or laparoscopy)—during removal of a fibroid, an incision is made in the uterus, and a barrier can be placed in between the uterus and the surrounding tissues to prevent adhesion; 2) abdominal—an adhesion barrier can be used to prevent peritoneal adhesions and therefore prevent intestinal obstruction; 3) cardiac—a barrier can be used to prevent post-operative adhesion after cardiac procedures; 4) cranial—a barrier can protect the exposed cortex during craniotomy to prevent the skull and the cortex from adhering; and 5) musculoskeletal—a barrier can prevent adherence of a tendon and the surrounding tissues.

Method for Sheet Formation and Adhesion Reduction

FIGS. 1a–1d illustrate an embodiment of a method for reduction of adhesion at a site of trauma. Alginate solution 1 is dispensed from a alginate solution dispenser 5 onto a substrate 7. As the solution 1 is dispensed, a film 20 of alginate solution 1 forms on the substrate 7. In some embodiments, the substrate 7 comprises glass, a polymer, aluminum or steel.

Figure 1A:
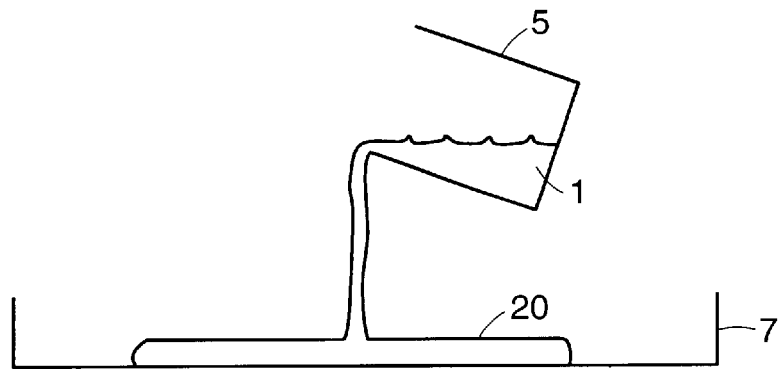
FIGS. 1a–1d are illustrations of a method of reducing adhesion at a site of trauma, according to an embodiment of the invention.
Figure 1B:
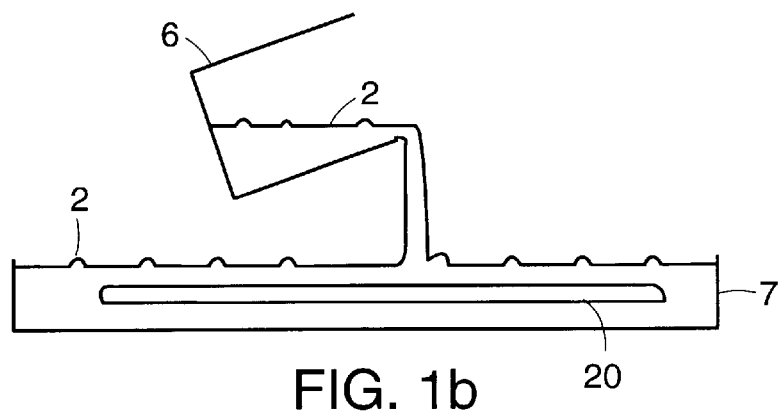

Referring to FIG. 1b, after formation of the film 20, cross-linking solution 2 is dispensed from a cross-linking solution dispenser 6. The cross-linking solution 2 contacts and surrounds the alginate solution film 20.

Figure 1C:
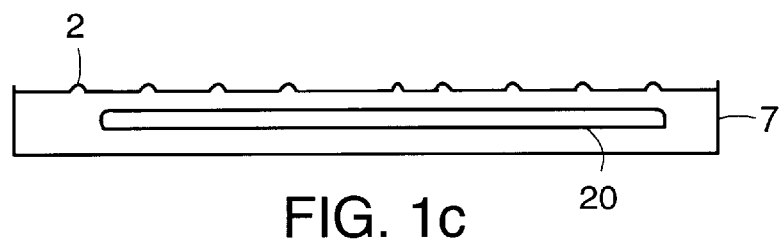
Figure 1D:

Referring to FIG. 1c, after dispensing the cross-linking solution 2, the cross-linking solution 2 is allowed to remain in contact with the alginate solution film 20 for a desired amount of time. The amount of time is varied to vary the degree of cross-linking and properties of the film 20. After sufficient cross-linking, a cross-linked mechanically stable sheet 10 is removed from contact with the cross-linking solution 2.

In one embodiment, the cross-linking solution 2 is poured onto the alginate solution film 20. In another embodiment, the film 20 forms when the alginate solution 1 is poured onto a film of the cross-linking solution 2.

Figure 2:
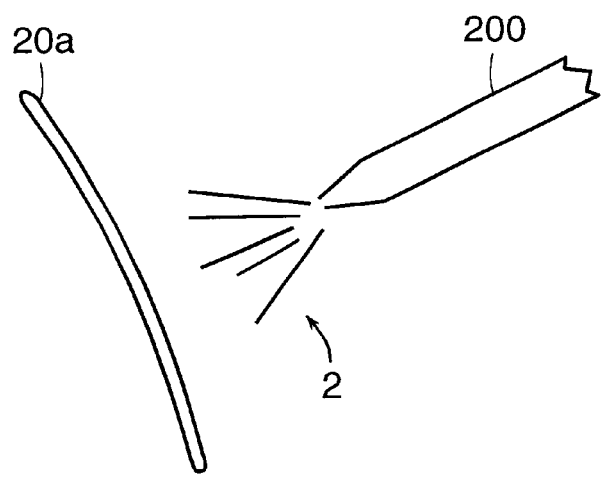
FIG. 2 illustrates spraying a cross-linking solution on a film of alginate solution.

FIG. 2 illustrates an alternative sheet 10 fabrication step that creates contact between an alginate film 20a and cross-linking solution 2. A cross-linking solution spray dispenser 200 sprays cross-linking solution 2 onto an alginate film 20a. The alginate film 20a in one embodiment is suspended while in another embodiment the film 20 rests on a substrate 7.

Figure 3:
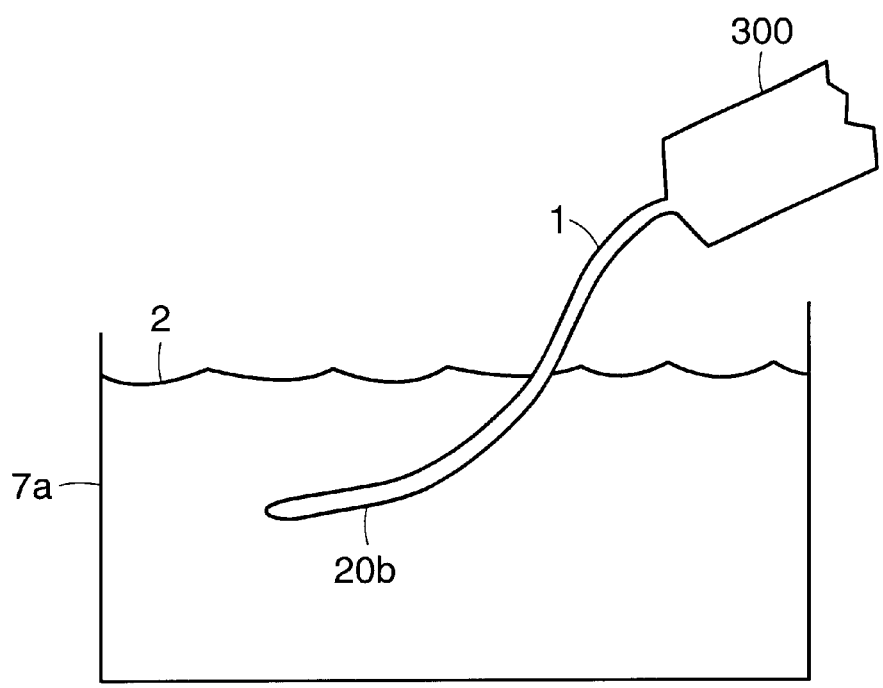
FIG. 3 illustrates contacting a film of alginate solution with a cross-linking solution by extrusion.

FIG. 3 illustrates another alternative sheet 10 fabrication step that creates contact between an alginate film 20 and cross-linking solution 2. Films 20b comprising alginate solution are extruded from an extrusion dispenser 300. The film 20b is immersed in a cross-linking solution 2 held in a vessel 7a.

In another embodiment, a substrate is dipped into alginate solution 20 to coat the substrate with an alginate film 20. The alginate film 20 is then contacted with cross-linking solution 2. This embodiment is particularly useful for fabrication of thin sheets 20.

In one embodiment, the alginate solution 1 comprises water and a water soluble alginate. In a preferred embodiment, the water soluble alginate is selected from the group consisting of sodium alginate, potassium alginate, magnesium alginate or propylene glycol alginate. In one embodiment, less than 40 wt % of the alginate solution 1 comprises sodium alginate.

In some embodiments, the cross-linking solution 2 comprises a divalent or trivalent metal salt. The salt can be selected, for example, from salts of the following metals: barium, calcium, copper, cobalt, aluminum, iron, boron, beryllium, lead and silver. In a preferred embodiment, less than 40 wt % of the cross-linking solution 2 comprises calcium chloride. Greater cross-linking solution 2 concentrations will cause more rapid cross-linking of the alginate film 20 while lower concentrations will cause slower cross-linking.

The quantity of cross-linking ions required to fully cross-link the alginate film 20 is a function of the quantity of functional groups in the film 20. Calcium ions, for example, react divalently with the guluronic acid part of alginate and monovalently with the mannuronic part or alginate. So, the amount of calcium required depends on the acid ratio.

In one embodiment, the contact time is varied to vary the degree or density of cross-linking in the sheet 10. This embodiment can be employed to control the sheet 10 flexibility and lifetime. Typical contact times are in the range of seconds up to one hour.

In another embodiment, the alginate solution 1 comprises a surfactant. A surfactant contributes to the ability of the alginate solution 1 to spread on the substrate 7, decreases surface tension of the sheet 10, and makes the sheet 10 more lubricious. Some surfactants can also act as a bactericide. For example, benzalkonium chloride is an effective wetting agent and antimicrobial agent. The alginate solution 1 can include nonionic or ionic surfactants, though preferably surfactants that do not interfere with the cross-linking reaction should be selected.

In another embodiment, the alginate solution 1 comprises alginic acid having an active ester or aldehyde at a carboxylate site, and the cross-linking solution 2 comprises a bifunctional cross-liner. The bifunctional cross-linker can comprise, for example, carbodiimide or dihydrazide.

After fabrication, a sheet 10 can be stored dry or wet, for example in sterile water, saline solution or water containing hygroscopic agents, such as glycerol, sorbitol, sucrose, and the like (it should be understood that a sheet 10 can be cut to any desired shape at any stage of use or before storage). In another embodiment, the sheet 10 is dried prior to storage and rehydrated prior to use. The sheet 10 can be sterilized as desired.

In some embodiments, the alginate solution film 20 is stored prior to contacting with the cross-linking solution 2. The film 20 can be dried prior to storage, for example by air-drying or freeze-drying.

The sheet 10 typically has a high water holding capacity. In some embodiments, the sheet holds up to approximately on third its weight in water. Other embodiments can hold over 99 % of their weight in water. For example, a sheet 10 experimentally prepared from a 4 wt % alginate solution held approximately 90 wt % water.

Figure 6A:
FIGS. 6a–6c are illustrations of fabrication of a sheet with a cross-link density that varies across the sheet thickness.
Figure 6B:
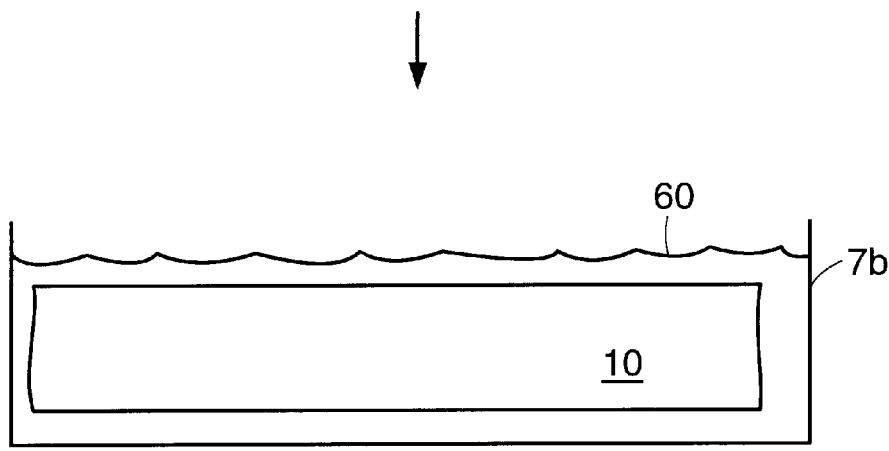
Figure 6C:
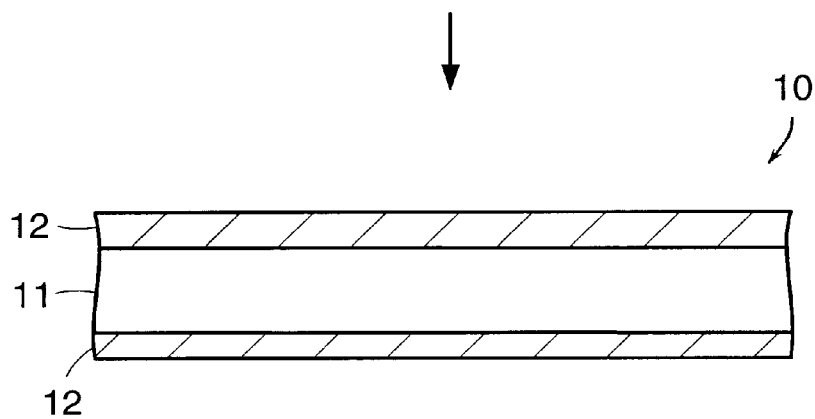

Referring to FIGS. 6a–6c, an embodiment is illustrated of a method of fabricating a sheet 10 with a cross-link density that varies across the sheet thickness 10. After formation of a sheet 10 (FIG. 6a) as discussed above, the sheet 10 is contacted with an ion-stripping agent 60 (FIG. 6b). The agent 60 reduces the cross-link density in outer portions 12 of the sheet 10 by stripping ions from the outer portions 12. This leaves an inner portion 11 of the sheet with a greater cross-link density than the outer portions 12 (FIG. 6c).

The ion-stripping agent 60 can comprise an ion-stripping solution held, for example, in a vessel 7b for immersion of the sheet 10. The ion-stripping solution can comprise, for example, EDTA or phosphate ions. In another embodiment, a cross-linked alginate sheet 10 is extruded and disposed in the ion-stripping solution. Agents 60 and their application are described in more detail below.

In another aspect of the invention, a method for in situ barrier formation is provided. In one aspect, the method comprises sequentially coating a trauma site with an alginate solution and a cross-linking solution. In one embodiment, a film of alginate solution is disposed at the site of trauma. Subsequently, a cross-linking solution is contacted with the film to form a cross-linked alginate barrier layer. In another embodiment, the crossing-linking solution is first coated on the desired tissue location followed by contacting with the alginate solution.

Cross-Linked Polymers

Some embodiments of the sheet 10 comprise cross-linkable polymers in addition to alginate. The anti-adhesion sheets 10 of one embodiment of the invention are fabricated from cross-linkable polymers which may be anionic or cationic in nature and include, but are not limited to, carboxylic, sulfate, hydroxy and amine-functionalized polymers, normally referred to as hydrogels after being cross-linked. The term "hydrogel" as defined herein is a cross-linked, water-insoluble, water-containing (e.g., hydrophilic) polymeric material.

Cross-linkable polymers used in some embodiments include one or a mixture of polysaccharides (e.g., alginic acid, pectinic acid, carboxy methyl cellulose, hyaluronic acid, heparin, heparin sulfate, chitosan, carboxymethyl chitosan, chitin, pullulan, gellan, xanthan, carboxymethyl starch, carboxymethyl dextran, chondroitin sulfate, cationic guar, cationic starch, as well as salts and esters thereof).

Polymers listed above which are not ionically cross-linkable can be used in blends with polymers which are ionically cross-linkable.

A preferred polymer is one based on alginic acid. These include sodium alginate, potassium alginate, magnesium alginate and propylene glycol alginate.

Ionic Cross-linking

The cross-linkable polymers according to one aspect of the present invention use ionic cross-linking. In some embodiments, they further use non-ionic (e.g., covalent) cross-linking. Ions used to ionically cross-link the polymers are polyions and may be anions or cations depending on whether the polymer is cationically or anionically cross-linkable.

Appropriate cross-linking cations include, but are not limited to, alkaline earth metals, such as calcium, magnesium, barium, strontium, and beryllium ions; transition metals, such as iron, manganese, copper, cobalt, zinc, and silver ions; other metallic elements, such as boron, aluminum, lead, and bismuth ions; and polyamonium ions, such as $^+H_3N$—$(CH_2)_n$—$NH_3^+$ or $^+H_3N$—$(CH_2)_n$—$CH((CH_2)_m$—$NH_3^+)((CH_2)_p$—$NH_3^+)$ where n is an integer ranging from 1 to 8, and m and p are integers ranging from 0 to 8 ions.

Anions are derived from polybasic organic or inorganic acids. Appropriate cross-linking anions include, but not limited to, phosphate, sulfate, citrate, borate, succinate, maleate, adipate and oxalate ions.

Preferred cross-linking cations are calcium, iron, and barium ions. The most preferred cross-linking cations are calcium and barium ions. The most preferred cross-linking anion is phosphate. Cross-linking may be carried out by contacting the polymers with an aqueous solution containing dissolved ions.

Sheet Mechanical Properties

In one aspect, the invention provides a suturable sheet 10. To demonstrate the mechanical stability of sheets 10 of the invention, four sample sheet 10 portions were prepared from alginate solution 1 of varying alginate concentration.

Table I gives mechanical pull strength test data for sheet 10 samples prepared from alginate solutions 1 of four different sodium alginate concentrations. Sheets 10 of approximately 0.5 mm thickness were permitted to fully cross-link prior to removal from a cross-linking solution 2 of 30 wt % calcium chloride. For mechanical testing, portions of each sheet 10 0.4 inch wide and approximately 0.5 inch long received conventional Instron pull testing to failure.

TABLE I

| alginate conc. (wt %) | load at tearing (lb) | displacement at tearing (inch) | tear force (lb/square inch) |
| --- | --- | --- | --- |
| 8 | 2.09 | 0.91 | 290 |
| 7 | 1.30 | 0.55 | 212 |
| 6 | 2.10 | 0.51 | 111 |
| 2 | 0.83 | 0.31 | 22 |

A sheet 10 preferably has a thickness in a range of 0.25 mm to 10 mm and more preferably in a range of 0.5 mm to 5 mm to provide both sufficient strength for suturing and sufficient flexibility to conform to the subject tissue.

Figure 5:
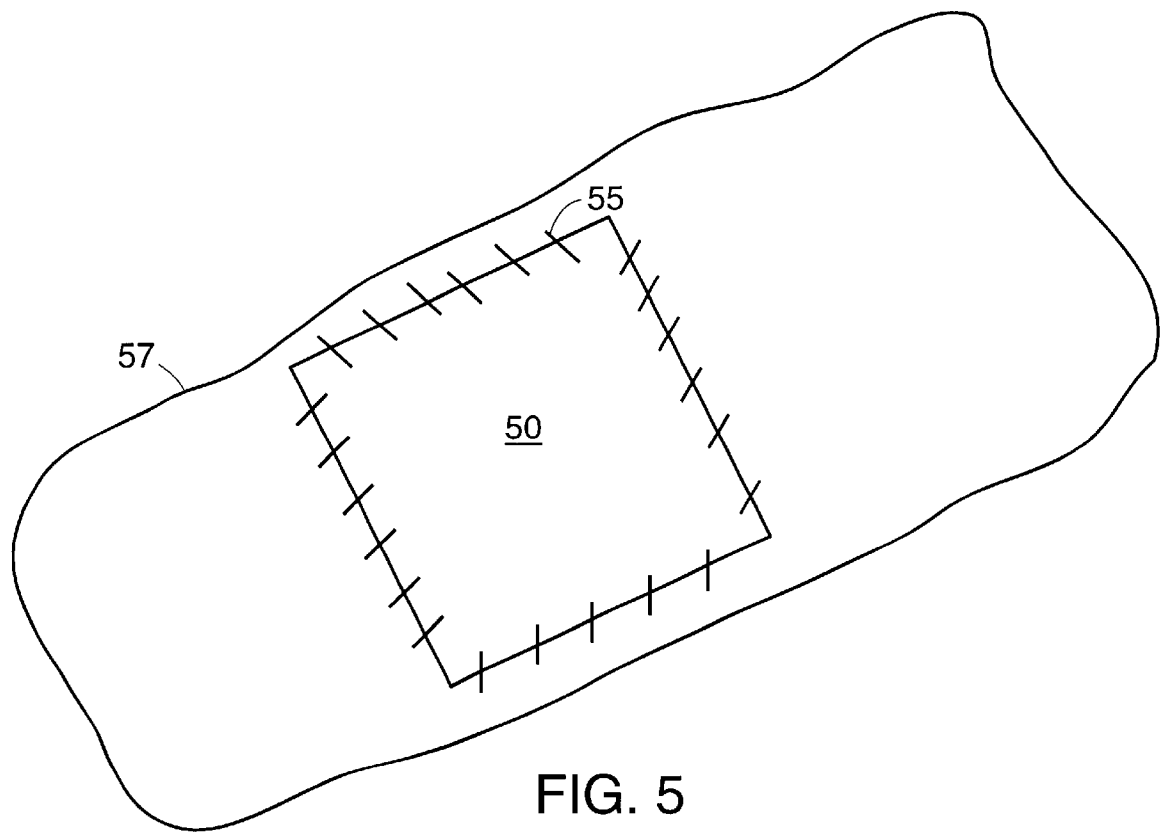
FIG. 5 is an illustration of an embodiment of a sheet sutured to a body tissue.

Referring to FIG. 5, suturing is illustrated. A portion of a sheet 50 has been fabricated in a square shape and attached with sutures 55 to tissue 57 at a site to be protected from formation of adhesion. The portion of a sheet 50 can be fabricated or cut at time of use to any convenient shape, for example, round, oval or polygonal.

Fillers

Figure 4:
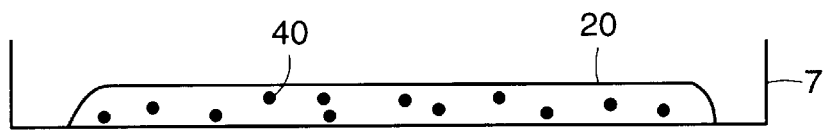
FIG. 4 is a cross-sectional illustration of an embodiment of a film that includes filler.

Referring to FIG. 4, in some embodiments the alginate solution 20 includes filler 40. The filler 40 can comprise particles, as illustrated in FIG. 4, or other material to modify various properties of the sheet 10. Fillers 40 that can serve in various embodiments are now described.

Radiopaque materials can be included in the alginate solution 20 to modulate the degradation rate, mechanical properties and increase the visibility under x-ray imaging of the sheet 10. Suitable radiopaque fillers include, but are not limited to, bismuth sub-carbonate, barium sulfate, bismuth oxychloride, tungsten, bismuth trioxide, tantalum, and the like. Such fillers 40 can facilitate visualization of the sheet 10 and a wound bed during healing through use of minimally invasive technology, such as fluoroscopic or x-ray imaging.

Other additives may be incorporated into the sheet 10 including, but not limited to, additives for medical treatment, such as antiseptics, antibiotics, contraceptives, nucleic acids [e.g., DNA (including genes, cDNAs and vectors), RNA, antisense molecules, ribozymes, PNA molecules], proteins (e.g., ligands, receptors, growth factors, cytokines, vascularizing agents, anti-vascularizing agents, antibodies, and the like), or medicines.

The hemostatic properties of the sheet 10 may be enhanced by the addition of anticoagulants, antithrombotic or other hemostatic compounds. For example, anticoagulants may be, but are not limited to, heparin, hirudins, thrombin, vasopressin and their derivatives.

The sheet 10 can comprise drugs. These drugs can include, for example, antibiotics such as β-lactams such as penicillins or cephalosporins, sulfonamides, quinolones floxacin and its derivatives, tetracyclines, macrolides such as erythromycin and its derivatives. These active substances may improve thrombogenicity and may significantly reduce healing time and reduce risk of infections.

In a further embodiment of the invention, filler 40 can be included to modify mechanical properties, such as elastic modulus, or hydrophobicity of the sheet 10. Appropriate fillers include biodegradable polymers, polysaccharides, polyesters and polymers possessing covalent cross-linking.

In one embodiment of the invention, biodegradable suture materials or other non-dissolvable filler materials, may be incorporated into the sheet 10 to provide additional mechanical strength. Biodegradable polymers include polyesters (such as polylactic acid (PLA), polyglycolic acid (PGA), polycaprolactone, copolymers of lactic acid, glycolic acid, and ε-caprolactone), other polysaccharides (such as cellulose and its water soluble derivatives or HA) or polymers with covalent cross-links (such as polymer derivatized with polyaziridine compounds). In some embodiments, biodegradable polymers are included in the alginate solution 1. In other embodiments, biodegradable polymers are applied to a surface of the sheet 10.

In another embodiment, the alginate solution 1 can comprise a biocompatible dye. Suitable dyes include FD&C blue No. 1, FD&C blue No. 2, FD&C green No. 3, FD&C green No. 5, FD&C yellow No. 5, FD&C yellow No. 6, FD&C yellow No. 10, β carotene, ginseng violet and food blue. Inclusion of such dyes in a sheet 10 can improve visibility of the sheet for positioning and repositioning.

In another embodiment, the filler 40 comprises a lifetime enhancer. A lifetime enhancer gradually releases cross-linking ions to replace those being lost from cross-linking sites in the sheet 10. While residing in a body, body fluids act to strip cross-linking ions from the sheet 10 (the action of ion stripping agents is discussed in more detail in a later section). Suitable lifetime enhancer materials include, for example, calcium sulfate, barium sulfate, strontium sulfate, copper sulfate, zinc sulfate and iron sulfate.

For example, the alginate solution 1 can include 10 wt % to 20 wt % calcium sulfate that will act as a cross-linking ion reservoir for the completed sheet 10. As calcium ion cross-linkers are lost from the sheet 10, additional calcium ions are derived from the reservoir until the reservoir is depleted.

Drug Delivery Device

In another aspect, the invention provides a drug delivery device. In one embodiment, the device comprises an cross-linked alginate container filled with a drug. The container is placed within a body to gradually release the drug.

Figure 7A:
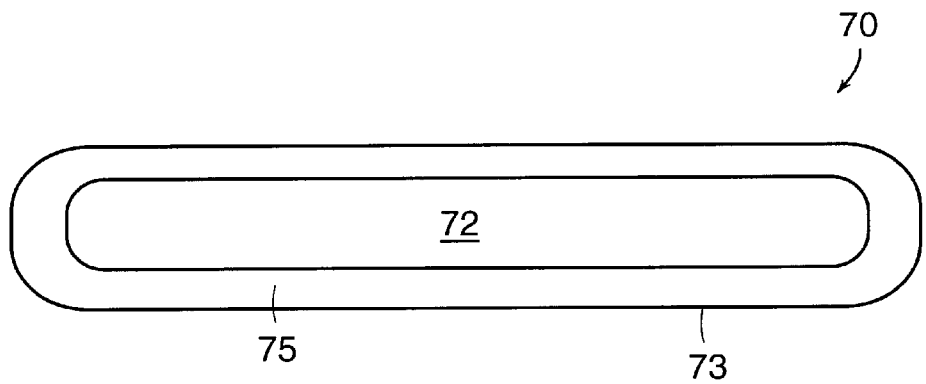
FIGS. 7a and 7b are illustrations of making a drug delivery device.
Figure 7B:
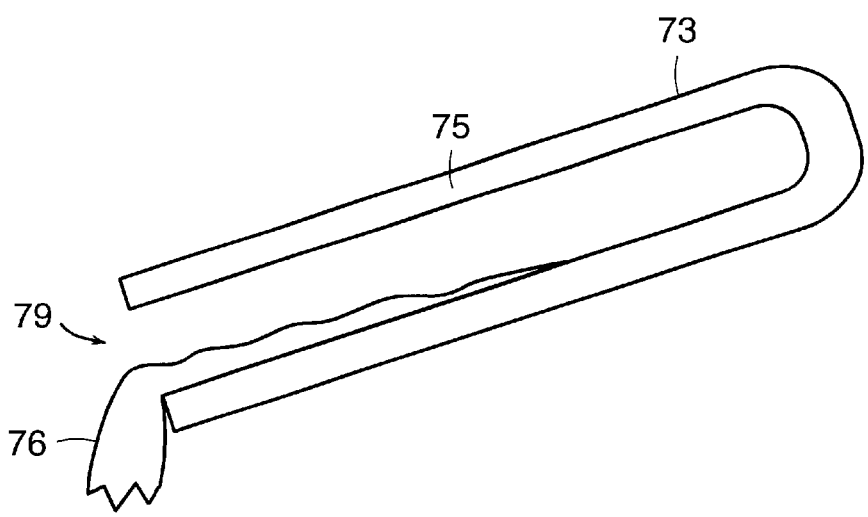

Referring to FIGS. 7a and b, an embodiment of a method for making a drug delivery device is illustrated. A film 70 is formed from an alginate solution 1, for example as described above. The outer surface 73 of the film 70 is contacted with cross-linking solution 2 to form a container 75. The container 75 comprises a cross-linked outer portion of the film 70 adjacent to the outer surface 73. An interior fluid portion 72 of the film 70, adjacent to an interior wall 77 of the container 75, remains substantially non-cross-linked, for example by limiting the cross-linking time or the available quantity of cross-linking ions in the cross-linking solution 2. The container 75 defines an interior space 78 that initially is filled with the substantially non-cross-linked interior fluid portion 72 of the film 70. The substantially non-cross-linked interior fluid portion 72 is drained from the container 75 through an opening 79 in the container 75.

In one embodiment, cross-linking solution 2 is inserted into the emptied interior space of the container 75 to cross-link the interior wall 77 of the container 75. In one embodiment, the container 75 is filled with a drug, sealed and inserted into a body for gradual release of the drug within the body.

Non-Ionic Cross-linking

In one embodiment of the invention, the cross-linkable polymers forming the sheet 10 of this invention include non-ionic cross-linking mechanisms to produce a sheet 10 having a higher cross-link density and improved mechanical properties, i.e., improved stiffness, modulus, yield stress and strength. This may be accomplished by additionally subjecting the ionically cross-linkable polymer to non-ionic cross-linking mechanisms such as high energy radiation (gamma rays) or treatment with a chemical cross-linking agent which reacts with groups present in the polymer such that covalent bonds are formed connecting different portions of the polymer or between polymer strands to form a web. Another non-ionic cross-linking mechanism useful with respect to some classes of hydrogel polymers is physical cross-linking. This is accomplished by crystal formation or similar association of polymer blocks such that the polymer molecules are physically tied together and prevented from complete dissolution. Non-ionic cross-linking may be carried out prior to, subsequent to, or concurrently with, ionic cross-linking.

A preferred method for non-ionic cross-linking is contact of an ionically cross-linkable polymer with a chemical cross-linking agent because the degree of cross-linking can be controlled mainly as a function of the concentration of the cross-linking agent. Suitable cross-linking agents are polyfunctional compounds preferably having at least two functional groups reactive with one or more functional groups present in the polymer. The cross-linking agent can contain one or more of carboxyl, hydroxy, epoxy, halogen, amino functional groups or hydrogen unsaturated groups, which are capable of undergoing facile nucleophilic or condensation reactions at temperatures up to about 100° C. with groups present along the polymer backbone or in the polymer structure. Suitable cross-linking reagents include polycarboxylic acids or anhydrides; polyamines; epihalohydrins; diepoxides; dialdehydes; diols; carboxylic acid halides, ketenes and like compounds. A preferred cross-linking agent is glutaraldehyde.

In one embodiment, cross-linkable polymers are provided which possess pendant organic acid functional groups which are covalently cross-linkable with polyfunctional cross-linking agents. In this embodiment of the invention, the covalent bonds between the cross-linking agents and the hydrophilic polymers are susceptible to hydrolysis in the body, releasing water-soluble components.

For purposes of the present invention, the term "organic acid functional group" includes any functional group which contains an acidic, ionizable hydrogen. Examples of such functional groups include free carboxylic, free sulfuric, and free phosphoric acid groups, their metal salts and combinations thereof. Such metal salts include, for example, (1) alkali metal salts, such as lithium, sodium and potassium salts, (2) alkaline earth metal salts, such as calcium or magnesium salts, and (3) quaternary amine salts of such acid groups, particularly quaternary ammonium salts.

One embodiment utilizes cross-linking agents that can form relatively weak covalent cross-linking bonds, so that these bonds can be "unzipped" or "de-cross-linked" within the body after a desired length of time. For example, polymers comprising covalent bonds that are easily hydrolysable at temperature and pH conditions inside the body can serve this purpose. Such polyfunctional covalent cross-linking agents include polyfunctional aziridines, polyfunctional carbodiimides, polyisocyanate, glutaraldehyde or other polyfunctional cross-linkers wherein the functional groups are capable of reacting with the organic acid groups, or any activated forms thereof.

In one embodiment, an alginate film 20 is dipped consecutively into two baths, each bath containing one type of cross-linking agent. For example, the entirety of the film 20 may be dipped into a first bath containing a solution of cross-linking cations to ionically cross-link a portion of the available cross-linking sites of the alginate; then, the at least partially ionically cross-linked film 20 is dipped into a second bath containing a solution of covalent cross-linking agent to covalently cross-link a portion, or all of, the remaining available cross-linking sites of the hydrophilic material. The extent of each type of cross-linking may be varied by varying the length of time of exposure of the sheet 10 to each type of cross-linking agent or, alternatively, by masking portions of the device.

Heterogeneous Polymers as Strengthening Filler

In one embodiment of the invention, the sheet 10 includes short segments of non-dissolvable, non-disintegratable polymer(s), or biodegradable suture material. The segments may be spaced at regular or irregular intervals. Such non-dissolvable polymer(s) or biodegradable suture material(s) provide added strength to a sheet 10 undergoing dissolution and/or disintegration.

Suitable non-dissolvable polymers include, but are not limited to, silicones, polyethylene oxides, polyvinyl alcohol, and the like. Suitable biodegradable suture materials are polymers of glycolic acid, ε-caprolactone, lactic acid, or copolymers thereof, and the like. Further embodiments utilize short or thin portions of non-dissolvable polymer, such as strings or meshes.

Modification of Cross-link Density

In one embodiment, displacement of cross-linking ions from the sheet 10 can be accomplished by flowing a solution containing a stripping agent around the sheet 10. The stripping agent serves to displace, sequester, or bind, the cross-linking ions present in the ionically cross-linked polymer, thereby removing the ionic cross-links. Some stripping agents are polyions capable of forming stable ionic bonds with the cations or anions disclosed above.

The choice of any particular stripping agent will depend on whether the ion to be displaced is an anion or a cation. If the cross-linking agent is a cation, then the stripping agent will be a polyanion, while if the cross-linking agent is an anion, the stripping agent will be a polycation. Suitable stripping agents include, but are not limited to, organic acids and their salts or esters, phosphoric acid and salts or esters thereof, sulfate salts and alkali metal or ammonium salts.

Examples of stripping agents include, but are not limited to, ethylene diamine tetraacetic acid, ethylene diamine tetraacetate, citric acid and its salts, organic phosphates, such as cellulose phosphate, inorganic phosphates, such as, pentasodium tripolyphosphate, mono and dibasic potassium phosphate, sodium pyrophosphate, phosphoric acid, trisodium carboxymethyloxysuccinate, nitrilotriacetic acid, maleic acid, oxalate, polyacrylic acid, as well as sodium, potassium, lithium, calcium and magnesium ions.

In one embodiment, the stripping step is accomplished by dipping or spraying the sheet 10 with an aqueous electrolyte solution for an appropriate time to selectively strip the cross-linking ions from the device. Some electrolytes for stripping are chlorides of monovalent cations such as sodium, potassium or lithium chloride, as well as other stripping salts described above. The concentration of the electrolyte salt in the solution may range from approximately 1 wt % up to the solubility limit. The solution may also contain plasticizing ingredients, such as glycerol or sorbitol, to facilitate inter- and intra-polymer chain motion for shaping of the sheet 10.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A method for forming a device for insertion into a body, comprising:
   providing a substrate;
   forming a film comprising an alginate solution on the substrate; and
   contacting the film with a cross-linking solution.

2. The method of claim 1, wherein forming the film comprises disposing the film on a portion of the substrate.

3. The method of claim 1, wherein the substrate has a first side and an opposed second side, and forming the film comprises disposing the film only on the first side of the substrate.

4. The method of claim 1, further comprising removing the film from the substrate after contacting the film, wherein the film is conformable to a body tissue.

5. The method of claim 4, further comprising altering a shape of the film after removing the film from the substrate.

6. The method of claim 1, wherein forming the film comprises dipping the substrate in a bath of the alginate solution.

7. The method of claim 1, wherein contacting the film with the cross-linking solution comprises spraying the cross-linking solution onto the film on the substrate.

8. The method of claim 1, wherein contacting the film with the cross-linking solution comprises dipping the substrate in a bath of the cross-linking solution.

9. The method of claim 1, wherein the alginate solution comprises one or more drugs.

10. The method of claim 1, wherein the substrate comprises a material selected from the group consisting of glass, polymer, aluminum and steel.

11. The method of claim 1, wherein the alginate solution comprises a filler.

12. The method of claim 11, wherein the filter comprises a radiopaque material.

13. A method for forming a medical device, comprising:
    forming a film from a solution comprising a cross-linkable polymer; and
    contacting the film with a cross-linking solution to form a cross-linked mechanically stable barrier for placement of the barrier at a site of trauma to provide an adhesion barrier.

14. The method of claim 13, wherein the cross-linkable polymer comprises a polysaccharide.

15. The method of claim 14, wherein the solution further comprises one or more drugs.

16. The method of claim 14, wherein the solution further comprises a filler.

17. A method for forming a device for use as an adhesion barrier, comprising:
    forming a film from a solution comprising a cross-linkable polymer; and
    exposing the film to at least one non-ionic cross-linking mechanism.

18. The method of claim 17, wherein the at least one non-ionic cross-linking mechanism comprises at least one of covalent bonds and physical cross-linking.

19. The method of claim 17, wherein the cross-linkable polymer comprises an alginate.

20. The method of claim 17, wherein the solution comprises more than one cross-linkable polymer.

21. A method for reducing adhesion at a site of trauma, comprising:
    disposing a film of a solution comprising a cross-linkable polymer at the site of trauma; and
    contacting the film disposed at the site of trauma with a cross-linking solution to form a cross-linked barrier layer.

22. The method of claim 21, whereby the barrier layer has a thickness in a range of 0.25 mm to 10 mm.

23. The method of claim 21, whereby the barrier layer has a tear strength in a range of 5 psi to 500 psi.

24. A method for reduction of adhesion at a site of trauma, comprising:
    disposing a film of cross-linking solution at the site of trauma; and
    contacting the film disposed at the site of trauma with a solution comprising a cross-linkable polymer to form a cross-linked barrier layer.

* * * * *

UNITED STATES PATENT AND TRADEMARK OFFICE
CERTIFICATE OF CORRECTION

PATENT NO. : 6,693,089 B1
DATED : February 17, 2004
INVENTOR(S) : Jianmin Li et al.

It is certified that error appears in the above-identified patent and that said Letters Patent is hereby corrected as shown below:

Column 1,
Line 43, before "ferric" change "a" to -- as --.

Column 6,
Line 2, change "cross-liner" to -- cross-linker --.
Line 18, before "third" change "on" to -- one --.

Column 7,
Line 27, after "but" insert -- are --.

Column 12,
Line 19, change "filter" to -- filler --.

Signed and Sealed this

Fifteenth Day of November, 2005

JON W. DUDAS
*Director of the United States Patent and Trademark Office*